(12) United States Patent
Ambrose

(10) Patent No.: US 7,813,940 B2
(45) Date of Patent: Oct. 12, 2010

(54) SYSTEM AND METHOD FOR ENABLING HEALTH CARE PROVIDERS TO EFFECT COMPENSATORY INVOICING OF PATIENTS WHO USE A COVERAGE ENTITY IN ADDITION TO THEIR HEALTH INSURER

(76) Inventor: Stephen David Ambrose, 9111 Carterham Rd., Richmond, VA (US) 23229

(*) Notice: Subject to any disclaimer, the term of this patent is extended or adjusted under 35 U.S.C. 154(b) by 770 days.

(21) Appl. No.: 11/749,160

(22) Filed: May 16, 2007

(65) Prior Publication Data

US 2008/0172250 A1  Jul. 17, 2008

Related U.S. Application Data

(63) Continuation-in-part of application No. 11/623,528, filed on Jan. 16, 2007.

(51) Int. Cl.
*G06Q 10/00* (2006.01)
(52) U.S. Cl. .......................................................... 705/2
(58) Field of Classification Search ........................ None
See application file for complete search history.

(56) References Cited

U.S. PATENT DOCUMENTS

| | | | |
|---|---|---|---|
| 5,235,507 A | 8/1993 | Sackler | |
| 6,330,551 B1 | 12/2001 | Burchetta | |
| 7,039,593 B2 | 5/2006 | Sager | |
| 2002/0035529 A1* | 3/2002 | Tooke, III | 705/35 |
| 2002/0077869 A1 | 6/2002 | Doyle | |
| 2004/0111302 A1 | 6/2004 | Falk | |
| 2004/0220865 A1 | 11/2004 | Lozowski | |
| 2005/0010454 A1 | 1/2005 | Falk | |

(Continued)

OTHER PUBLICATIONS

Shapiro, Richard N., "Recovering Medical Expenses—Are Double and Triple Recoveries Permitted?", Mar. 7, 2006, Website Link: http://virginiabeach.injuryboard.com/motor-vehicle-accidents/recovering-medical-expensesare-double-or-triple-recoveries-permitted.php.

*Primary Examiner*—Jason M Borlinghaus

(57) ABSTRACT

A system and method is provided for compensatory invoicing of a patient for health care services rendered by a Health Care Provider. The system and method enables a Health Care Provider to obtain payment of Full Rates for services rendered to a patient in circumstances where a Health Insurance Entity provides less than full-rate compensation (e.g., compensation at Contracted Rates) to the Health Care Provider AND the patient has been reimbursed additionally by another payment party for claims already paid for by the Health Insurance Entity. In one implementation, the patient contracts with the Health Care Provider to ensure that the Health Care Provider is fully compensated for the services rendered after the patient receives payments from a tortfeasor and/or First and/or Third Party Payment Entity (e.g., an auto insurance carrier, worker's compensation insurance carrier, Medpay, PIP etc.) for the services. The invention tracks claim(s) filed by the patient against the tortfeasor and/or First and/or Third Party Payment Entity and tracks payments) made by the tortfeasor and/or First and/or Third Party Payment Entity to the patient. The patient and/or the First and/or Third Party Payment Entity is then billed for the difference in payments made to the Health Care Provider by the Health Insurance Entity, effecting compensatory invoicing for a Full Rate fee chargeable by the Health Care Provider in cases when a tortfeasor and/or First and/or Third Payment party has reimbursed the patient for similar services as already reimbursed by the Health Insurance Entity.

29 Claims, 3 Drawing Sheets

U.S. PATENT DOCUMENTS

| | | |
|---|---|---|
| 2005/0080653 A1 | 4/2005 | Stemple |
| 2005/0091080 A1 | 4/2005 | Biats |
| 2006/0116914 A1 | 6/2006 | Stemple |
| 2006/0136264 A1 * | 6/2006 | Eaton et al. .................... 705/2 |

* cited by examiner

SYSTEM AND METHOD FOR ENABLING HEALTH CARE PROVIDERS TO EFFECT COMPENSATORY INVOICING OF PATIENTS WHO USE A COVERAGE ENTITY IN ADDITION TO THEIR HEALTH INSURER

FIELD OF THE INVENTION

This application is a continuation-in-part of U.S. patent application Ser. No. 11/623,528, filed on Jan. 16, 2007 entitled "System and Method For Enabling Health Care Providers To Effect Compensatory Invoicing of Patients Who Use A Coverage Entity In Addition To Their Health. Insurer" filed by inventor Stephen D. Ambrose.

The invention relates to systems and methods for health providers and related parties to effect compensatory invoicing of patients who utilize a coverage entity with respect to their health care service bills, in addition to their health insurance, pursuant to a Collateral Source Rule or otherwise.

BACKGROUND OF THE INVENTION

In the current health care arena, physicians, hospitals, and other health care providers (hereinafter the "Health Care Provider") contract with health insurance companies, managed care organizations ("MCOs"), or other health insurance providers (hereinafter the "Health Insurance Entity"). Typically, both a Health Care Provider and a patient have a contractual relationship with a Health Insurance Entity. In general, when a patient visits an "in-network" Health Care Provider, the patient receives services which are subsequently billed to the Health Insurance Entity by the Health Care Provider. The Health Insurance Entity is typically the primary payer for services and will cover necessary treatment and care for the patient's various health problems, including acute injuries.

Upon contracting with the Health insurance Entity, the Health Care Provider generally agrees to accept contracted rates set by the Health Insurance Entity (hereinafter "Contracted Rates"). These Contracted Rates are typically lower than the normal, full-rate fees charged by the Health Care Provider (hereinafter "Full Rates") for the delivery of a variety of billable services. In return, the Health Care Provider is given access to the Health Insurance Entity's patients, some of whom may be assigned to the Health Care Provider. The Health Care Provider also agrees that, during the term of the patient's coverage by the Health insurance Entity, if the patient is to be billed for the Health Care Provider's services directly for any reason, the Health Care Provider can only bill at the Contracted Rates for the services performed, provided that these are services normally paid for by the Health Insurance Entity.

In most Health Insurance Entity/Health Care Provider contracts, the Health Care Provider is prohibited from billing a patient for any amounts attributable to the difference between the Health Care Provider's Full Rates and the Contracted Rates. This type of billing, is known commonly as "Balance Billing" i.e., billing the patient for the balance between the Contracted Rates and the Full Rates). The difference in rates can sometimes he quite large. Thus, while a Health Care Provider obtains some benefits from contracts with Health insurance Entities, certain financial drawbacks exist.

When a patient visits a Health Care Provider for medical attention of injuries, symptoms, or disease stemming from an accident or other event for which there is an applicable liability insurance product and/or an individual, group or business who is determined responsible in a court of law or otherwise, for the patient's injury or reason for obtaining medical attention (hereinafter known as "tortfeasor"), there may be instances when one or more parties other than a Health Insurance Entity, such as a first and/or third party payer as well as compensation paid by a tortfeasor to the patient and/or their Agent may provide payments for the Health Care Provider's services. For example, in the case of an auto accident, the first party payer may be the auto insurance company for any injured individual through an attached medical payment rider, regardless of fault in the accident (hereinafter "Medpay") or the insurer for any auto insurance rider known as Personal Injury Protection (hereinafter "PIP"). Medpay, PIP insurers and other first party payment entities can be referred to as a first party payer (hereinafter "First Party Payment Entity"). Another example is the patient or their use of an attorney, agent or legal representative (hereinafter "Agent") in utilizing their health care bills in part or full, so as to obtain a legal judgment and/or agreement with the tortfeasor, allowing for payment to the patient and/or their Agent. An example of a third party payer may be the automobile (or other) liability insurance company for the driver (or other entity) who was "at-fault" or responsible for the Covered Event, e.g. for causing the auto (or other) accident and the injuries for which the injured, non-responsible party received treatment. Third party payers, for example, may include auto insurance carriers, liability, property & casualty and worker's compensation insurance carriers, and other third party payers, among other types of entities (hereinafter "Third Party Payment Entity"). For example, if a patient visits a Health Care Provider because he or she was in an automobile accident, the patient's Health Insurance Entity may be billed, and the patient's Health Insurance Entity may subsequently pay medical bills to the Health Care Provider who provided services to the patient. In some instances, the Health Insurance Entity may elect to seek reimbursement for monies paid for services from a First and/or Third Party Payment Entity who has also paid monies for similar health services, through a process known as subrogation.

However, in many jurisdictions (e.g., states), there is a legal doctrine known as the "Collateral Source Rule" that, allows an injured, patient and/or their Agent to submit medical bills to a First and/or Third Party Payment Entity, even if the bills have already been paid by the Health Insurance Entity to the respective health care provider(s). The Collateral Source Rule prohibits the admission at trial of evidence that a patient's injuries were already compensated from a health insurance policy or other source of compensation. For example, in a personal injury case, evidence that a Plaintiffs medical bills were paid by his or her medical insurance are not admissible. This is largely because the Collateral Source Rule is intended to promote justice and assess remedies for fault of the tortfeasor (the entity or entities that caused the injury).

Additionally, some insurance or other payment sources that pay for an injured party's damages may gain a lien or right of subrogation in any ultimate recovery by or on behalf of the injured party. In these circumstances, the injured patient must pay back the party with the subrogation right, who had previously paid on charges from Health Care Providers), assuming the patient received additional payment for the same billed services by other payment sources other than the party with the subrogation rights.

One problem with this system is that complete and full rate payment may not be made to the Health Care Providers for services performed and billed. Agents and/or injured parties however, can submit the Health Care Provider's medical bills as part of a lawsuit and/or directly to a tortfeasor and/or to a First and/or Third Party Payment Entity and receive compensation at Full Rates, even if the medical bills were already paid. Thus, the Health Care Provider receives payment at the lower Contracted Rates, while the patient and/or their Agent through utilizing the provider's bills, can receive compensation paid by a tortfeasor to the patient and/or their Agent as well as by a First and/or Third Party Payment Entity at the higher Health Care Provider's Full Rates.

Additionally, many Health Care Provider/Health Insurance Entity contracts provide for a waiver of subrogation on the Health Care Provider's part. Subrogation is a legal concept where one entity assumes the legal rights of another entity for whom the first entity has paid expenses or a debt on their behalf. For example, when an insurer is required to pay a claimant a sum of money, the insurer usually is allowed to sue in the name of the claimant against any person who was responsible for the loss. This concept enables an insurance company to sue on behalf of its insured if it is required to pay the insured for a loss caused by another entity. Subrogation is generally considered in most legal systems to form part of the law of restitution by preventing unjust enrichment. In other words, subrogation prevents the subrogor (e.g., the patient) from receiving/utilizing funds from the subrogee (e.g., the health care insurer), and then still claiming the original sum of money from the tortfeasor (e.g., the entity that caused the accident). Pursuant to the waiver of subrogation, the Health Insurance Entity may be able to recover any payments made for services provided to a patient following an auto accident or other Covered Event, provided that the First and/or Third Party Payment Entity paid monies for the same set of services. Thus, even if the Health Insurance Entity receives payment at the Full Rates, the Health Care Provider gets nothing more than the Contracted Rates. In this sense, patients, attorneys and other parties can leverage the Health Care Provider's efforts to financially benefit. for themselves, many times at the full fee rates, while the Health Care Provider receives only the Contracted Rates.

These and other drawbacks exist with known billing practices.

SUMMARY OF THE INVENTION

The invention addressing these and other drawbacks relates to a system and method for enabling a Health Care Provider to effect compensatory invoicing of patients for a Covered Event in instances where the patient has contracted with a Health Insurance Entity for provision of health care services at a Contracted Rate and additionally, there exists compensation paid by a tortfeasor to the patient and/or their Agent and/or a responsible First and/or Third Party Payment Entity who is liable for payment due to the Covered Event.

According to an aspect of the invention, a Health Care Provider may take one or more steps to ensure that it is in a legal position to effect compensatory invoicing of a patient to effectively bill a patient, while honoring the Health Care Provider/Health Insurance Entity Contract (under certain circumstances) by enforcing a billing arrangement which would enable the Health Care Provider to be paid their Full Rate when a patient or their Agent receives compensation paid by a tortfeasor and/or First and/or Third Party Payment Entity other than their Health Insurance Entity.

For example, in one implementation, a Health Care Provider, prior to rendering services to a new (or current) patient who is seeking care stemming from a Covered Event, requires the patient to sign a legal contract between the patient and the Health Care Provider, specifically outlining the billing policies of the Health Care Provider, where the contract includes a provision entitling the Health Care Provider to be entitled to their Full Rate (not the Contracted Rate) if the patient and/or their Agent uses the Health Care Provider's bills for compensation by submitting the bills to a tortfeasor via a lawsuit or otherwise and/or First and/or Third Party Payment Entity (e.g., an entity other than the Patient's Health Insurance Entity).

Once a signed contract is in place by and between the patient and the Health Care Provider, the Health Care Provider provides necessary services to the patient in the ordinary course, bills the Health Insurance Entity at the Contracted Rates, and receives payment from the Health Insurance Entity for the rendered services at the Contracted Rates.

Subsequently, the Health Care Provider (or someone on behalf of the Health Care Provider) may monitor a variety of sources to determine whether the patient and or their Agent has had compensation paid by a tortfeasor and/or a First and/or Third Party Payment Entity relating to services provided by the Health Care Provider. Monitored sources may, for example, include Court records (electronic or otherwise) as well as the use of various health provider and billing databases, many of which are currently known (but used for other purposes). This may also include providing a questionnaire with the paperwork which the patient fills out and signs at the Health Care Provider's office prior to, during or subsequent to treatment, asking if the injury or reason the patient is seeking care stems directly from an accident or Covered Event, and if so, identification of any pending lawsuits or submission of provider's health bills to a tortfeasor and/or First and/or Third Party Payment Entities. The requesting of treatment records, bills, statements, etc. either by the patient or a representative (agent) of the patient may also be a trigger, alerting the Health Care Provider and related staff that compensatory invoicing may be appropriate.

Monitoring may further be performed manually and/or electronically at predetermined intervals or otherwise. Additionally, the patient may also allow the Health Care Provider to bill the First and/or Third Party Payment Entity as well as collect from the patient and/or their Agent any compensation paid by a tortfeasor to the patient and/or their Agent. Whichever the case, the Health Care Provider (or agent) enforces the billing contract between the Health Care Provider and the patient to effect compensatory invoicing and collect the difference between the Full Rates and the Contracted Rates in appropriate circumstances.

According to an aspect of the invention, a system is provided, which enables the review and subsequent auditing of past patient records by comparing them against a monitoring system allowing the Health Care Provider to effect compensatory invoicing and collect any difference(s) between their Full Rate(s) and Contracted Rate(s) for rendered services if the patient and/or their agent/representative uses the Health Care Provider's bills and has compensation paid by a tortfeasor and/or First and/or Third Party Payment Entity (e.g., an entity other than the Patient's Health insurance Entity).

In one implementation, the system may comprise a computer system, and the computer system may further host, interface with, or otherwise enable access to a billing management application for tracking information/contracts for those patients who are seeking payment for healthcare services (either in full or in part) from a tortfeasor and/or a First and/or Third Party Payment Entity (other than the Patient's Health Insurance Entity). The billing management application may comprise an "add-on" application to existing or subsequently developed billing applications, or may comprise a separate "stand-alone" application.

In one implementation, the computer system (and billing application) may be in operative communication with one or more external data sources (e.g., legal databases that include information on Court proceedings and other data sources). Information gathered from the one or more external data sources may be maintained, for example, in one or more associated databases. The information may comprise, among other things, information on claims filed by patients (contracting with the Health Care Provider) and/or their Agent against any tortfeasor and/or First and/or Third Party Payment Entity (other than the patient's Health Insurance Entity) and the status of any such proceedings related to the claims. The information may also comprise data on any payment-related activities that have occurred between contracted patients and any tortfeasor and/or First and/or Third Party Payment Entity.

For each patient contracting with the Health Care Provider, die billing management application may generate reports on-demand, or at pre-determined intervals, that include the current status of any efforts by the particular contracting patient to recover money from a patient and/or Agent in lieu of a tortfeasor's compensation as well as a First and/or Third Party Payment. Entity (other than the patient's Health insurance Entity).

In one implementation, if a patient has been compensated by a tortfeasor and/or First and/or Third Party Payment Entity, the billing management application may generate, pursuant to the contract between the patient and the Health Care Provider, a bill for the difference between the Health Care Provider's Full Rates (for services rendered by the Health Care Provider to the patient) and the payment received by the Health Care Provider from the Health Insurance Entity at the Contracted Rates.

Various other objects, features, and advantages of the invention will be apparent through the detailed description of the preferred embodiments and the drawings attached hereto. It is also to be understood that both the foregoing general description and the following detailed description are exemplary and not restrictive of the scope of the invention.

DETAILED DESCRIPTION OF THE PREFERRED EMBODIMENTS

Figure 1:
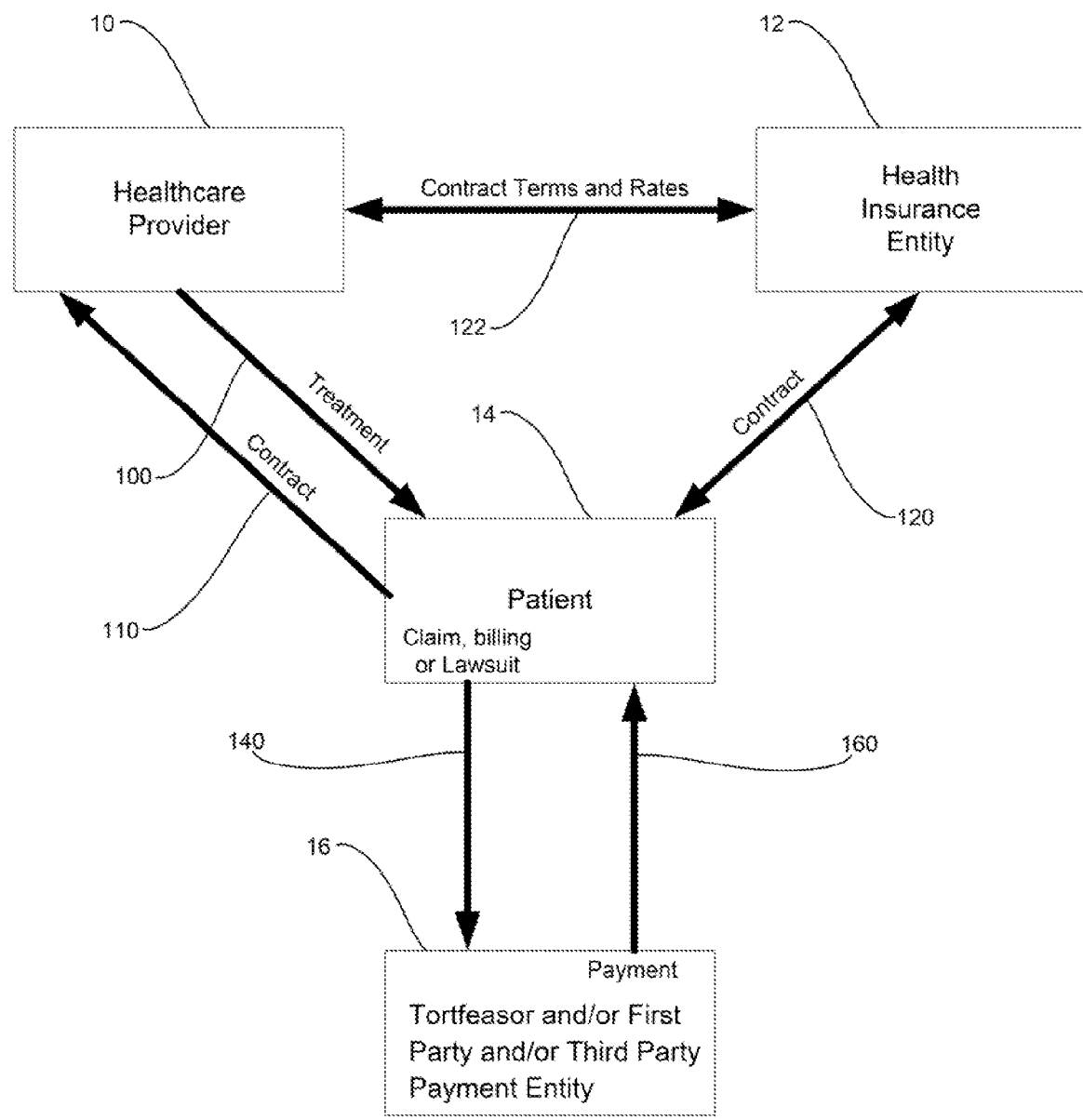
FIG. 1 is an exemplary illustration of a block diagram illustrating the inter-relationships between parties, according to an aspect of the invention.

The invention will now be described in detail with reference to the drawing figures, which are provided as illustrative examples so as to enable those skilled in the art to make and use the invention. Notably, the drawing figures and accompanying text (and examples) provided herein are not meant to limit the scope of the invention. In the drawing figures, like components, services, applications, and operations are designated by like reference numerals throughout the various drawing figures. Where certain elements of the invention can be partially or fully implemented using known components, only those portions of such known components that are necessary for an understanding of the present invention may be described, and detailed descriptions of other portions of such known components may be omitted so as not to obscure the invention. Further, the invention encompasses present and future known equivalents to the components referred to herein by way of illustration.

According to an aspect of the invention, a system and method are provided for enabling a Health Care Provider to effect compensatory invoicing of a patient for a Covered Event in instances where the Health Care Provider has contracted with a Health Insurance Entity for provision of health care services to patients at a Contracted Rate and die patient and/or their Agent has been compensated by a tortfeasor and/or there is a First and/or Third Party Payment Entity liable for payment doe to the Covered Event.

With reference to FIG. 1, the invention enables a Health Care Provider 10 to effect compensatory invoicing of a patient and recoup Full Rates for treatments and services 100 rendered to a patient 14 in those instances wherein patient 14 chooses to also collect payment 140 from a tortfeasor and/or a First and/or Third Party Payment Entity 16 in addition to their Health Insurance Entity 12 for treatment or services 100 rendered.

Healthcare Provider 10 may comprise, without limitation, a physician, hospital, or other provider of medical treatment or services. Health Insurance Entity 12, as noted above, may comprise, without limitation, a health insurance company, an MCO, or other provider of health or medical insurance. Examples of First Party Payment Entities include entities through which the patient has MedPay, PIP or other applicable coverage (other than the patient's Health Insurance Entity). Examples of Third Party Payment Entities 16 may include, but are not limited to collateral sources such as auto insurance carriers, liability, property & casualty and worker's compensation insurance carriers. Examples of tortfeasors are those individuals, groups and businesses, which have caused tort or civil wrong to others. This includes responsibility for various types of accidents through negligence; in addition, applicable torts also include malpractice, personal injury, product liability, drug & material liability, intentional harm, etc.

By way of background, when Health Care Provider 10 enters into a contract 122 with Health Insurance Entity 12, Health Care Provider 10 typically agrees to contracted billing rates (defined above as the "Contracted Rate") for providing treatment and services 100 that is often lower than the customary Full Rate charged by Health Care Provider 10 for the service 100. Further, the contract terms 122 between Health Insurance Entity 12 and Health Care Provider 10 typically require Health Care Provider 10 to honor a no-Balance Billing policy that prohibits Health Care Provider 10 from recovering directly from the patient the difference between the Full Rate and Contracted Rate fees for services 100 rendered to patient 14 by Health Care Provider 10. This prohibition also applies to services provided in relation to injuries received in an auto accident, work-related accident, etc. provided that the Health Insurance Entity is the sole source of payment for the service 100.

According to one implementation of the invention, however, a system and method is provided whereby Health Care Provider 10 can identify billing arrangements, inform patient 14 of billing policies, and subsequently enforce a billing contract 110 that would enable the Health Care Provider 10 to be paid at a Full Rate when patient 14 receives compensation 160 from a collateral source (e.g., tortfeasor and/or a First and/or Third Party Payment Entity 16) in addition to the patient's contracted 120 Health Insurance Entity 12.

Figure 2:
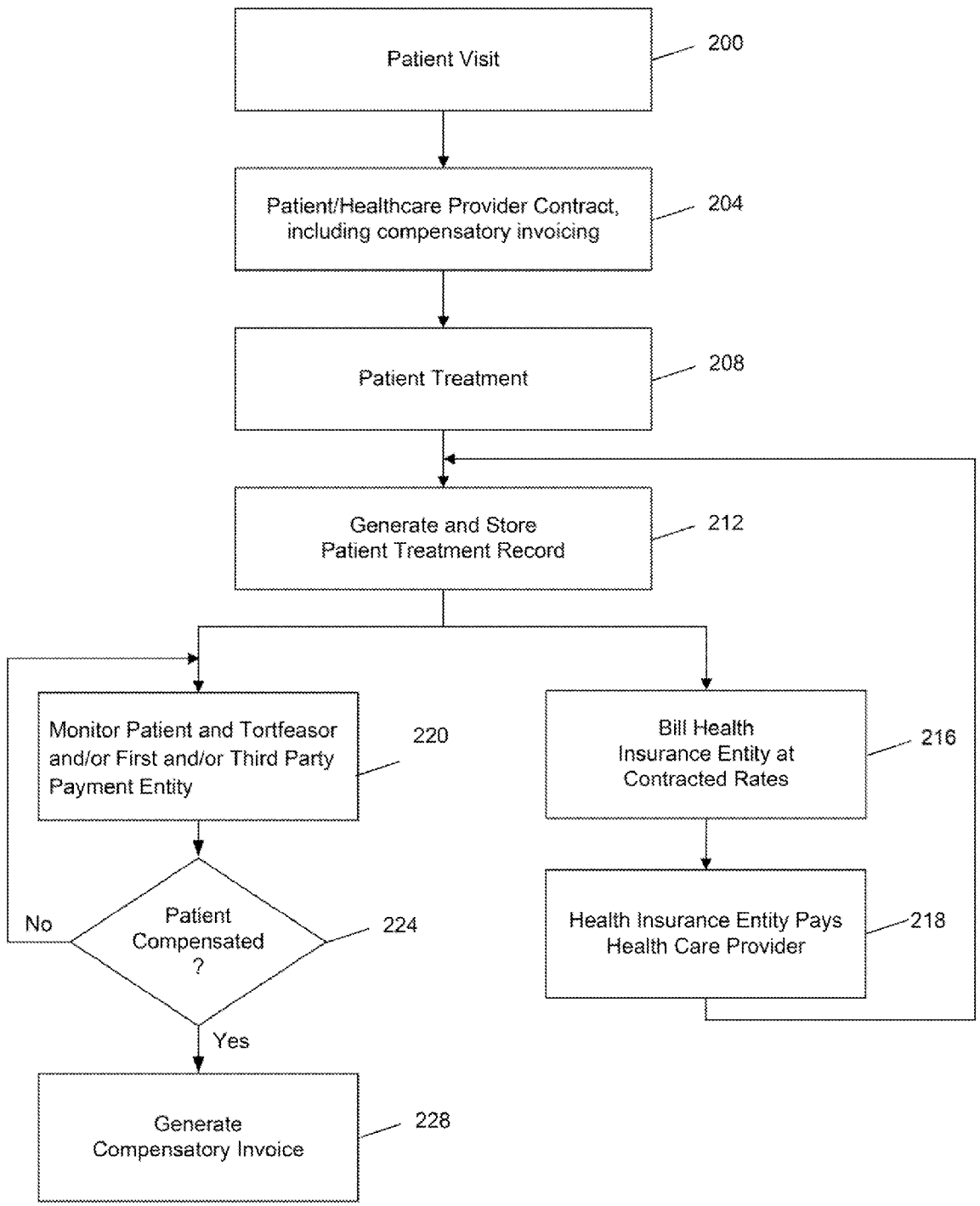
FIG. 2 is an exemplary illustration of a processing flowchart, according to an aspect of the invention.

Referring to FIG. 2, an exemplary flowchart of processing operations will now be described. In an operation 200, a Health Care Provider may receive a visit from a new or existing patient seeking medical attention due to injuries, symptoms, or disease stemming from an accident or other event for which a tortfeasor and/or liability insurance product is applicable (defined above as a "Covered Event"), and wherein payment from tortfeasor and/or First and/or Third Party Payment Entity (other than the patient's Health Insurance Entity) may be anticipated.

In an operation 204, the patient may be provided with a contract to sign specifying the Health Care Provider's billing policies where more than one payment entity is or may be anticipated. The terms of the contract may dictate that the Health Care Provider is entitled to effect compensatory invoicing of the patient to effectively receive payment at the Full Rate (not the Contracted Rate) if the patient uses the Health Care Provider's bills for compensation from a tortfeasor and/or First and/or Third Party Payment Entity in addition to (or other than) the patient's Health Insurance Entity. However, if the patient is not able to chooses not to utilize any additional sources of payment (other than the patient's Health Insurance Entity), even if such payments are available, the Health Care Provider must accept the Contracted Rate from the Health Insurance Entity and not Balance Bill the patient.

Once a signed contract is in place by and between the patient and the Health Care Provider, the Health Care Provider provides necessary services to the patient in the ordinary source, in an operation 208.

In an operation 212, a record of the treatment or services rendered to the patient is made, including billed charges related to treatment/services 208. The record may be maintained via one or more computer systems as a part of the Health Care Provider's billing system and/or through an entity related to the Health Care Provider (i.e., a Medical Billing Company) and/or through an unrelated third party specializing in retrieving such information through data mining or other investigative techniques (hereinafter "Investigative Company"). As detailed below, the one or more computer systems may be configured to track payments made responsive to and/or identify billing payment party sources for the treatment due to the Covered Event. Payments may be made by any combination of the patient's Health insurance Entity and collateral sources (e.g., a tortfeasor and/or First, and/or Third Parry Payment Entity).

In an operation 216, the Health Care Provider bills the Health Insurance Entity at the Contracted Rates. In operation 218 the Health Insurance Entity pays the Health Care Provider for the rendered services at the Contracted Rates. This payment may be recorded and associated with the patient, record and/or Health Care Provider billing system.

In an operation 220, the Health Care Provider (or someone on behalf of the Health Care Provider) may monitor a variety of sources to determine whether the patient and/or the patient's Agent has filed a claim against a tortfeasor and/or a First and/or Third Party Payment Entity and/or received compensation from a tortfeasor and/or a First and/or Third Party Payment Entity relating to services provided by the Health Care Provider due to a Covered Event.

Operation 220 may include, for example, an electronic (or manual) search of databases or other information sources to determine whether the patient has received or should have received payment based on the Health Care Provider's billing. Monitored sources may, for example, include Court records (electronic or otherwise). It may also include the review of a questionnaire completed by patient prior to treatment, asking if the injury or reason the patient is seeking care stems directly from an accident or other Covered Event. The requesting of treatment records, bills, statements, etc. either by the patient or a representative (agent) of the patient may also be a trigger, alerting the Health Care Provider and related staff (or system if the request is electronically implemented) to the potential ability to effect compensatory invoicing of a patient. Other data sources may be monitored and steps taken to assist the Health Care Provider in identifying when it can effect compensatory invoicing of a patient. Monitoring may be performed manually and/or electronically at pre-determined intervals or otherwise. Any number of configurations and techniques may be implemented. An electronic search may employ techniques including, but not limited to, data mining to obtain information such as claims and payments records associated with the patient. Electronic searches may be conducted to audit records associated with patients having past treatment from Health Care Provider who qualified as injured persons entitled to compensation from plural payers.

In addition, in operation 220, reports may be generated on-demand, or at pre-determined intervals, that include information on any claims/lawsuits filed by patients against any tortfeasor and/or First and/or Third Party Payment Entity (other than the patient's Health Insurance Entity) and the status of any such proceedings related to the claims. The information may also comprise data on any payment-related activities that have occurred between contracted patients and any tortfeasor and/or corresponding First and/or Third Party Payment Entities.

In an operation 224, a determination may be made as to whether the patient and/or their Agent has been compensated by a tortfeasor and/or a First and/or Third Party Payment Entity for any relevant activity identified in operation 220. If, in operation 224, it is determined that the patient and/or their Agent has been compensated by a tortfeasor and/or a First and/or Third Party Payment Entity for a Covered Event, a compensatory invoice may be generated in an operation 228. The compensatory invoice may be generated for any difference(s) between the Full Rate(s) of the Health Care Provider and the Contracted Rate(s) for rendered services reimbursed by the Patient's Health Insurance Entity. The bill may be provided to any combination of the patient, a representative of the patient authorized to receive such billing, and/or any person or entity likely to be in possession of monies collected on behalf of the patient.

If a determination is made, in operation 224, that the patient has not yet been compensated by a tortfeasor and/or a First and/or Third Party Payment Entity for a Covered Event, then monitoring may continue in operation 220.

It should be recognized that, generally, the prohibition against Health Care Providers Balance Billing their patients, found in typical Health Care Provider/Health Insurance Entity contracts is not violated where the Health Care Provider/patient contract is directed to collect monies via compensatory invoicing of a patient due to payments received by or on behalf of the patient from a tortfeasor and/or a First and/or Third Party Payment Entity, which arises when the patient utilizes the bills of the Health Care Provider to collect payments a second or third time (through the Collateral Source Rule with the First and/or Third Party Payment Entity). Unlike Balance Billing, which is when Health Care Providers collect the difference between the Full and Contracted rates when the patient only utilizes a Health Insurance Entity for payment of services, in Compensatory Invoicing, the Health Care Provider is collecting the difference not from the patient directly, but from First and/or Third Party Payment Entities and/or a patient and/or a patient's Agent who has received payments from a tortfeasor and/or a First and/or Third Party Payment Entities in direct relation to said services performed by the Health Care Provider for the patient.

Figure 3:
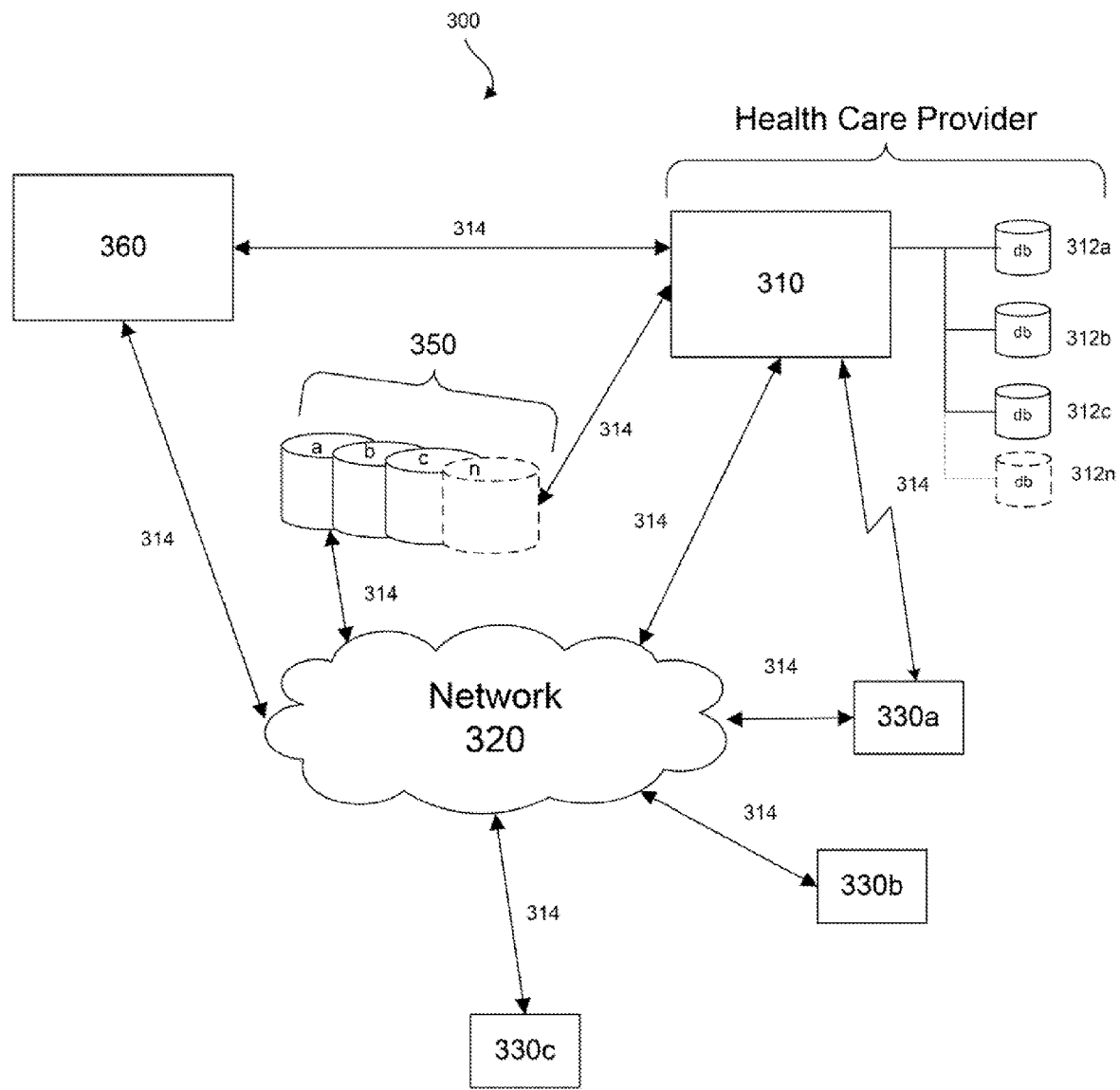
FIG. 3 is an exemplary Illustration of a system diagram, according to an aspect of the invention.

According to an aspect of the invention, as illustrated in FIG. 3, a system 300 may be provided for, among other things, enabling a Health Care Provider to effect compensatory invoicing of a patient for a Covered Event in instances where the patient has contracted with a Health Insurance Entity for provision of health care services at a Contracted Rate and a tortfeasor and/or a First and/or Third Party Payment Entity is liable for payment due to the Covered Event.

In one implementation, system 300 may comprise a computer system 310, which is maintained by or on behalf of, associated with, or otherwise accessible by a Health Care Provider. Computer system 310 may comprise a server, personal computer, or other computing device capable of executing software applications. As an exemplary, non-limiting illustration, computer system 310 may comprise a server which may be or include, for instance, a workstation running Microsoft Windows™ NT™, Microsoft Windows™ 2000, Unix, Linux, Xenix, IBM, AIX™, Hewlett-Packard UX™, Novell Netware™, Sun Microsystems Solaris™, OS/2™, BeOS™, Mach, Apache, OpenStep,™ or other operating system or platform.

In one implementation, computer system 310 may host a billing management application for, among other things, tracking information/contracts for those patients who are seeking payment for healthcare services (either in full or in part) from a tortfeasor and/or a First and/or Third Party Payment Entity (other than the patient's Health Insurance Entity). In some implementations, the billing management application may comprise a "stand-alone" application. Alternatively, the billing management application may comprise an "add-on" application to existing or subsequently developed billing applications.

In an alternative implementation, the billing management application may be hosted by a computer system (e.g., one or more servers) 360 associated with a service provider, and computer system 310 may be directly linked to computer system 360 via a communications link 314. Alternatively, computer system 360 (and the billing management application) may be accessed over a network 320 (via a communications link 314) by a user of computer system 310.

Network 320 may include, but is not limited to, any one or more of, for instance, the Internet, an intranet, a PAN (Personal Area Network), a LAN (Local Area Network), a WAN (Wide Area Network), a SAN (Storage Area Network), or a MAN (Metropolitan Area Network).

Communications link 314 may include, but is not limited to, any one or more of, for instance, a copper telephone line, a Digital Subscriber Line (DSL) connection, a Digital Data Service (DDS) connection, an Ethernet connection, an Integrated Services Digital Network (ISDN) line, an analog modem connection, a cable modem connection, or a wireless connection.

According to an aspect of the Invention, one or more databases (312a, 312b, . . . 312n) may be operatively connected to the Health Care Provider computer system 310. The one or more databases (312a, 312b, . . . 312n) may be locally accessible by computer system 310. In alternative implementations, security or other operational considerations may dictate that the one or more databases (312a, 312b, . . . 312n) be physically maintained in a different location from computer system 310, and accessed through a private network. Other configurations may be implemented.

The one or more databases (312a, 312b, . . . 312n) may be, include, or interface to, for example, an Oracle™ relational database sold commercially by Oracle Corporation. Other databases, such as Informix™, DB2 (Database 2) or other data storage or query formats, platforms, or resources such as OLAP (On Line Analytical Processing), SQL (Standard Query Language), a SAN (storage area network), Microsoft Access™ or others may also be used, incorporated, or accessed into the invention.

Patient data, billing records, and information corresponding to various Health Insurance Entities and Third Party Payment Entities are non-limiting examples of the types of information that may be stored in one or more databases (312a, 312b, . . . 312n). Such information might also be non-electronic and be stored, monitored and interpreted appropriately.

According to an aspect of the invention, the billing management application may be utilized to generate and/or update patient records for each patient seeking treatment from a Health Care Provider. As will be appreciated by those having skill in the art, patient records may include data including, but not limited to, personal information, medical history information, billing and payment information, information on Health Insurance Entities, and a record of treatment and/or services rendered.

According to an aspect of the invention, if a patient is seeking medical attention to injuries, symptoms, or disease stemming from an accident or Covered Event for which a tortfeasor and/or liability insurance product is applicable, and wherein payment from a tortfeasor and/or a First and/or Third Party Payment Entity (other than the patient's Health Insurance Entity) may be anticipated, the billing management application (or other application) may generate a contract for execution by the patient and the Health Care Provider. As described in detail above, the terms of the contract may dictate that the Health Care Provider be entitled to receive payment at a Full Rate (not the Contracted Rate) if the patient uses the Health Care Provider's bills for compensation from a tortfeasor and/or a First and/or Third Party Payment Entity in addition to (or other than) the patient's Health Insurance Entity. Additionally, or as part of the contract, the application may generate a form or provisions that require the patient to identify any tortfeasor and/or First and or Third Party that may be liable to the patient for the Covered Event.

Once a signed contract is in place by and between the patient and the Health Care Provider, a copy of the contract may be scanned (or otherwise duplicated electronically) and appended to the patient's record for later retrieval via the billing management application. Via Optical Character Recognition (OCR) or other technology specific information from the contract and/or questionnaire may be entered into a database for subsequent tracking by or on behalf of the Health Care Provider to assist in effecting compensatory invoicing of a patient, when appropriate. Manual entry of information into a database may also be performed.

Once a patient has been treated, the patient's record may be updated with information corresponding to the treatment or services rendered to the patient. The billing management application may then handle the billing of the patient's Health Insurance Entity (at the Contracted Rates). Where appropriate (e.g., when the questionnaire indicates there may be a tortfeasor and/or a First and/or Third Party Payment Entity, when the treatment/services are due to a Covered Event or when otherwise appropriate), the patient's record may be identified or "flagged" by the billing management application as a matter requiring the monitoring (or tracking) of liability claims associated with the treatment and/or subsequent monitoring and/or data mining may generate an alert to flag the patient record as described elsewhere herein to determine when and/or whether the Health Care Provider may effect compensatory invoicing of the patient.

According to an aspect of the invention, as part of the follow-up for "flagged" patient records (and/or to generate flags), the billing management application (or a service provider) may monitor a variety of external data sources (350a, 350b, . . . 350n) to determine whether the patient has filed a claim against a tortfeasor and/or a First and/or Third Party Payment Entity and/or received compensation from a tortfeasor and/or a First and/or Third Party Payment Entity relating to services provided by the Health Care Provider. The flag may be cleared when payment on the compensatory invoice has been made and/or received and/or when a compensatory invoice is issued.

The one or more external data sources (350a, 350b, . . . 350n) may be directly or indirectly networked to computer system 310, or operatively connected to computer system 310 via any suitable network 320. According to one implementation, one or more external data sources (350a, 350b, . . . 350n) may comprise one or more computers (e.g., servers), databases, Internet web sites, or other host sites or applications, or any combination thereof, and may comprise publicly-accessible data and/or private data requiring subscriptions and/or access authorization. In certain instances, such authorization may be granted by the patient (or an agent authorized to act on the patient's behalf), or by another person or entity.

The one or more external data sources (350a, 350b, . . . 350n) may be utilized to gain access to information related to, among other things, medical diagnostic codes, unedited medical claims. Court records of legal proceedings including docketing information and decisions in related cases in State and Federal Courts. The information may further comprise information identifying the patient, the patient's legal representative including attorney-at-law, attorney-in-fact, legal guardian, and estate. The one or more external data sources (350a, 350b, . . . 350n) may also comprise information identifying persons, entities and organizations involved in transfers of payments associated with the performance of services by the Health Care Provider, including escrow agents, the patient's legal representatives, and insurance companies.

In one implementation, the billing management application may execute search functions, data-mining functions, or other functions to acquire relevant information from the one or more external data sources (350a, 350b, . . . 350n). A Health Care Provider or other user may cause the billing management application to execute these functions on-demand, or at pre-determined intervals. Acquired data may then, for example, be stored in the one or more databases (312, 312b, . . . 312n) associated with computer system 310.

In an alternative implementation, any of the aforementioned information may also be provided to the billing management application via transfer of media including, for example, Bin-Ray disk, DVD, CD-ROM, memory stick, tape, disk, and/or other suitable removable media, wireless means, as well as paper records. In this implementation, the Health Care Provider may cause the billing management application to request updates and new records from external information sources as necessary to maintain consistency and currency of information in the one or more associated databases (312a, 312b, . . . 312n).

Certain implementations may employ a combination of on-line access (to external data sources (350a, 350b, . . . 350n), and removable media to access information necessary to track third party billing and payments.

According to an aspect of the invention, the billing management application can respond to queries and provide reports to, among other persons or entities. Health Care Providers and Health Care Providers' staff. In certain implementations, reports may be provided on demand, upon the occurrence of certain events at desired intervals, including, for example, daily, weekly, and/or monthly intervals or at other times. Reports may be customizable, and may identify the status of billing processes (Including compensatory invoicing) for one or more patients, and may identify delinquencies and delayed payments.

In one implementation, reports may also identify events for patients that may be of particular significance to the Health Care Provider including, for example, patient and/or patient's Agent filing a lawsuit and/or receiving a judgment against a tortfeasor, filing of claims against First and/or Third Party Payment Entities, entries of payments to the patient from a tortfeasor and/or First and/or Third Party Payment Entities and other events or information.

Reports may be provided in any number of customizable formats to users of computer system 310. Additionally, reports may be accessible by (or provided in an outbound communication) to users via any number of client devices (330a, 330b, . . . 330n) in any number of formats. Examples of client devices (330a, 330b, . . . 330n) may include, but are not limited to, personal computers, portable computers, PDAs (personal digital assistants), workstations, mobile phones, web-enabled mobile phones, WAP devices, web-to-voice devices, or other devices.

In one implementation, information may be further provided by an interactive voice response (IVR) system configured to access the billing management application upon the request of authorized users, and provide information via audio output.

According to an aspect of the invention, upon confirmation of payment by a tortfeasor and/or a First and/or Third Parry Payment Entity to patient, the billing management application may generate a compensatory invoice for the patient and/or any agent of the patient, (e.g., their attorney) for the difference between the Full Rate and the Contracted Rate.

Those having skill in the art will appreciate that the invention described herein may work with various system configurations. Accordingly, more or less of the aforementioned system components depicted in FIG. 3 (and described above) may be used and/or combined in various implementations.

Additionally, according to a business method, a service provider may provide and/or use the described systems and/or perform described services on behalf of multiple Health Care Providers to implement one or more of the steps described herein with respect to: i) identifying when treatment/services rendered by a Health Care Provider relates to a Covered Event; ii) identify one or more tortfeasors) and/or First and/or Third Party Payment Entities; iii) determine when compensatory invoicing is appropriate; and/or iv) effect, when appropriate, compensatory invoicing of the patient on behalf of the relevant Health Care Provider. According to this business method the service provider may bill the Health Care Provider in a number of different ways including fixed fees per month (or other period); a fixed fee per patient/covered event monitored; based on a percentage of any recoveries received due to the compensatory invoicing of any patient; and/or otherwise.

Other embodiments, uses and advantages of the invention will be apparent to those skilled in the art from consideration of the specification and practice of the invention disclosed herein. The specification should be considered exemplary only, and the scope of the invention is accordingly intended to be limited only by the following claims.

What is claimed is:

1. A billing and payment collection method utilized by a health care provider to bill and collect payment associated with treatment of a patient, the method comprising:

transmitting a health care service bill from the health provider to a patient's health insurance plan for health care services provided to the patient by the health care provider, wherein the health care service bill is for the normal and full charge for the rendered health care services;

accepting a contractual rate payment from the health insurance plan in response to the transmitted health care service bill, wherein the contractual rate payment is lower than the health care provider's normal and full charge for the rendered health care services;

determining that an additional payment party exists, which is not the patient's health insurance plan, wherein the additional payment party is responsible to pay the patient for the health care service bill, when submitted by the patient, irrespective of the patient's health insurance plan paying the health care provider for the same health care service bill;

entering into a private billing contract between the health care provider and the patient for differential monies, wherein the differential monies are the difference between the normal and full charge for the rendered health care services, and the contractual rate payment made by the health insurance plan in response to the health care service bill, wherein the differential monies are only due to the health provider upon the patient submitting the health care service bill to an additional party and receiving payment therefrom;

submitting via the patient the health care service bill to the additional payment party;

receiving, by the patient, from the additional payment party monies in response to the submitted health care service bill, wherein the received monies includes differential monies;

billing and collecting the differential monies from the patient by the health care provider based upon the private billing contract; and wherein the prior steps are performed by one or more computers.

2. The method of claim 1, wherein the billing and collection for the health provider is performed by a third party.

3. The method of claim 1, wherein the patient submits the health care service bill to the additional payment party via an attorney or legal representative.

4. The method of claim 1, wherein the health care service bill relates to an injury claim involving the patient.

5. The method of claim 1, wherein the private billing contract is made prior to any care being rendered by the health care provider to the patient.

6. The method of claim 1, wherein the health care provider is a provider selected from a group consisting of a health system, hospital, surgical center, rehab facility, physician's practice, ambulatory center, medical service business, imaging center, outsourced diagnostic testing company, home health agency, therapy clinic, chiropractic and any non-medical practitioner and facility legally allowed to perform health care services.

7. The method of claim 1, wherein the health care services are services selected from a group consisting of consultation, examination, treatment, surgery, use of pharmaceutical products, home health, therapy, imaging, laboratory services and use of medical equipment.

8. The method of claim 1, wherein the additional payment party is based upon an insurance rider selected from a group consisting of a Med Pay, No-Fault, Uninsured Motorist, Underinsured Motorist and Personal Injury Protection riders on an automobile insurance of the patient.

9. The method of claim 1, wherein the additional payment party is based on a liability insurance product representing the at-fault party, selected from a group consisting of general liability, professional liability, auto liability, employer liability, public liability and product liability.

10. The method of claim 1, wherein the additional payment party is a party selected from a group consisting of an individual, group, business, partnership, limited liability company, insurance coverage, association, municipality, county, state, and federal government entity.

11. The method of claim 4, wherein the injury claim is based upon an injury selected from a group consisting of an auto accident, work-related injury, soft-tissue injury, liability on premises, liability due to environment, product defect, pharmaceutical product, birth injury, assault, slip, fall, circumstance relating negligence and medical malpractice.

12. The method of claim 1, wherein the private billing contract is a medical lien between the provider and patient.

13. The method of claim 1, wherein the submission of the health care service bill to the additional payment party by the patient is conducted via an attorney or legal representative.

14. The method of claim 1, wherein the differential monies exclude monies paid to the health care provider, said excluded monies selected from a group consisting of a health insurance co-payment, a health insurance deductible and co-insurance.

15. The method of claim 4, wherein the health care provider collects differential monies relating to the injury claim from the patient via an attorney or legal representative of the patient.

16. A computerized investigation method to determine whether differential monies legally owed to a health care provider by a patient are in the possession of the patient, the method comprising:

transmitting a heath care service bill from the health provider to the patient's health insurance plan for health care services provided to the patient by the health care provider, wherein the health care service bill is for the normal and full charge for the rendered health care services accepting a contractual rate payment from the health insurance plan in response to the transmitted health care service bill, wherein the contractual rate payment is lower than the health care provider's normal and full charge for the rendered health care services;

determining an additional payment party exists, which is not the patient's health insurance plan, wherein the additional payment party is responsible to pay the patient for the health care service bill, when submitted by the patient, irrespective of the patient's health insurance plan paying the health care provider for the same health care service bill;

entering into a private billing contract between the health care provider and the patient, wherein existing differential monies are deemed owed from the patient to the health care provider, wherein the differential monies are the difference between the normal and full charge for the rendered health care services, and the contractual rate payment made by the health insurance plan in response to the health care service bill, wherein the differential monies are only due to the health provider upon the patient submitting the health care service bill to an additional party and receiving payment therefrom;

submitting via the patient the health care service bill for the rendered health care services to the additional payment party;

determining by the health care provider, through an investigation, that the patient received monies from the additional payment party in response to the submitted health care service bill, wherein the received monies include the differential monies; and wherein the prior steps are performed by one or more computers.

17. The method of claim 16, wherein the additional payment party is based upon an insurance rider selected from a group consisting of a Med Pay, No-Fault, Uninsured Motorist, Underinsured Motorist and Personal Injury Protection riders on an automobile insurance of the patient.

18. The method of claim 16, wherein the additional payment party is based on a liability insurance product representing the at-fault party, selected from a group consisting of general liability, professional liability, auto liability, employer liability, public liability and product liability.

19. The method of claim 16, wherein the additional payment party is a party selected from a group consisting of an individual, group, business, partnership, limited liability company, insurance coverage, association, municipality, county, state, and federal government entity.

20. The method of claim 16, wherein the injury claim is based upon an injury selected from a group consisting of an auto accident, work-related injury, soft-tissue injury, liability on premises, liability due to environment, product defect, pharmaceutical product, birth injury, assault, slip, fall, circumstance relating negligence and medical malpractice.

21. The method of claim 16, wherein the private billing contract is a medical lien between the provider and patient.

22. The method of claim 16, wherein the submission of the health care service bill to the additional payment party by the patient is conducted via an attorney or legal representative.

23. The method of claim 16, wherein the investigation for the health care provider is performed by a third party.

24. The method of claim 16, wherein the patient submits the health care service bill to the additional payment party via an attorney or legal representative.

25. The method of claim 16, wherein the health care service bill relates to an injury claim involving the patient.

26. The method of claim 16, wherein the private billing contract is made prior to any care being rendered by the health care provider to the patient.

27. The method of claim 16, wherein the health care provider is a provider selected from a group consisting of a health system, hospital, surgical center, rehab facility, physician's practice, ambulatory center, medical service business, imaging center, outsourced diagnostic testing company, home health agency, therapy clinic, chiropractic and any non-medical practitioner and facility legally allowed to perform health care services.

28. The method of claim 16, wherein the health care service is a service selected from a group consisting of consultation, examination, treatment, surgery, use of pharmaceutical products, home health, therapy, imaging, laboratory services and use of medical equipment.

29. The method of claim 16, wherein the differential monies exclude monies paid to the health care provider, said excluded monies selected from a group consisting of a health insurance co-payment, a health insurance deductible and co-insurance.

* * * * *